Aug. 24, 1943. C. MALLERIN Plant Pat. 599
ROSE PLANT
Filed Jan. 19, 1943
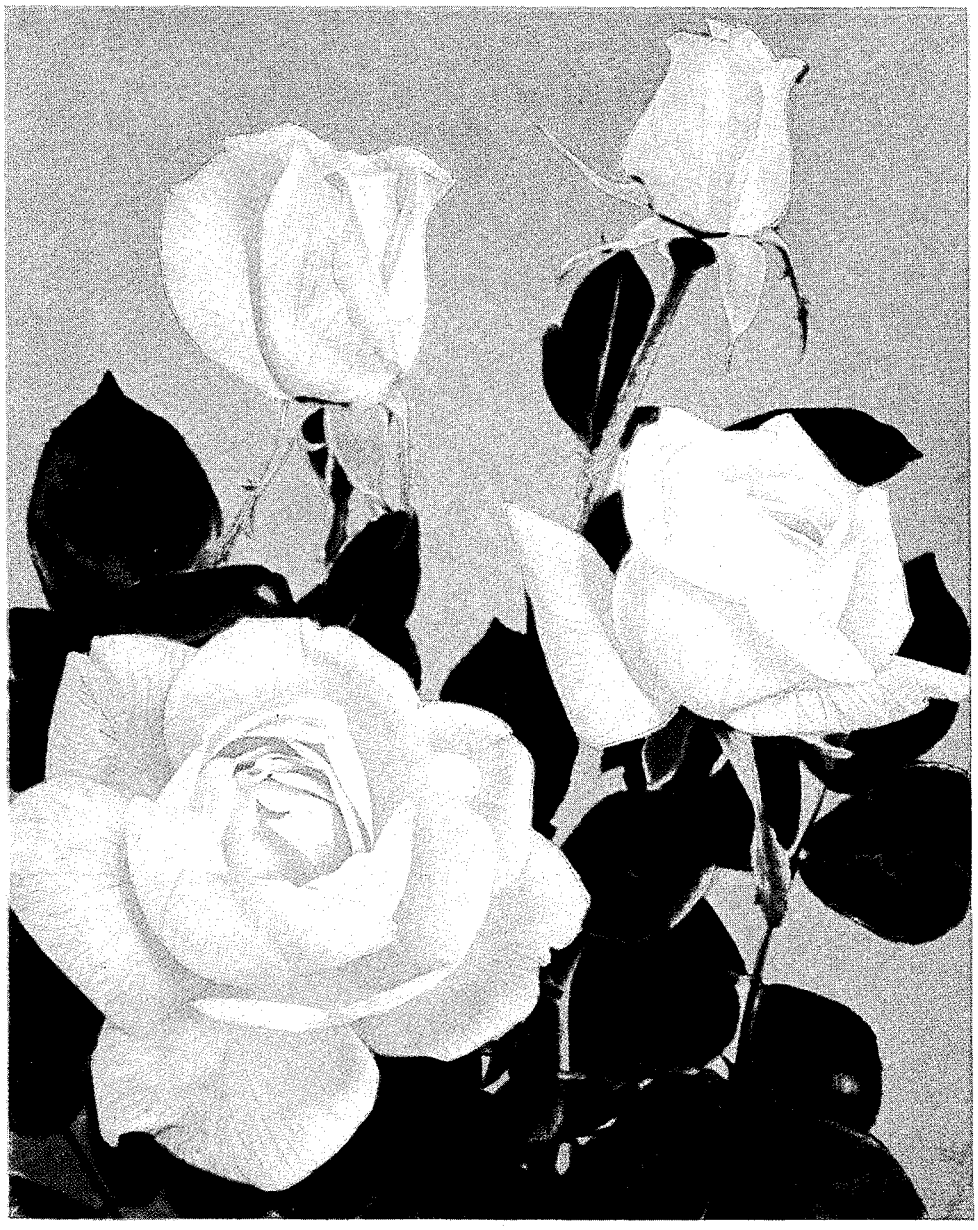
Inventor
Charles Mallerin
By Robb & Robb
Attorneys Patented Aug. 24, 1943

UNITED STATES PATENT OFFICE

599

ROSE PLANT

Charles Mallerin, Varces, France, assignor to
The Conard-Pyle Company, West Grove, Pa.

Application January 19, 1943, Serial No. 472,891

1 Claim. (Cl. 47—61)

The present invention relates to a new and distinct variety of rose plant, the result of a definite effort to produce a new rose having the desirable growth characteristics of its parents together with novel color combinations of flowers.

This new variety possesses vigor of growth to an unusual degree and this habit taken with its production of highly colored bloom, having a multicolored effect, has resulted in a lusty plant of extraordinary attractiveness and unlike any other known to me.

The following is a detail description of the new variety, color terminology being in accord with Ridgway's Color Standard:

Type: Hardy; tall; bush; outdoor; seedling; for garden decoration.
Class: Hybrid Tea.
Parentage: Seedling:
*Seed parent.*—Luis Brinas.
*Pollen parent.*—Brazier.
Propagation: Holds its distinguishing characteristics through succeeding propagations by budding, which is the only method employed up to the present time.

*Flower*

Locality where grown: West Grove, Pennsylvania.
Flowers borne: Singly and several to stem; on normal, long stems.
Quantity of bloom: Free; outdoors.
Continuity: Intermittent.
Fragrance: Moderate; spicy.
Bud:
*Peduncle.*—Medium long; medium heavy; medium stiff; Oil Green, Plate V; medium rough; numerous Argus Brown, Plate III, prickles.
*Before calyx breaks.*—*Size*—medium large. *Form*—pointed; ovoid; with an inconspicuous neck; with foliaceous appendages on the surface of the bud; with slender bristle-like foliaceous parts extending beyond the tip of the bud equal to one-fourth or more of its length.
*As calyx breaks.*—*Color*—Lemon Chrome, Plate IV, veined and suffused Rose Doree, Plate I.
*As first petal opens.*—*Size*—medium large. *Form* — ovoid. *Color* — outside — Lemon Chrome, Plate IV, veined and suffused Spinel Red, Plate XXVI. Inside—Chalcedony Yellow base, Plate XVII, and Spinel Red, Plate XXVI, veined Tyrian Rose, Plate XII. *Opening*—opens up well.
Bloom:
*Size.*—When fully open, four to four and one-half inches.
*Petalage.*—Very double, usually with stamens showing; from thirty to thirty-five petals.
*Form.*—Cupped; high center, at first; becoming open, cupped high centered; petals remaining at first loosely rolled outward; becoming later, at maturity, nearly flat rolled outward.
Petals: Leathery; inside and outside satiny.
*Shape.*—Outside—obovate; scalloped with apex flat with one notch. Intermediate—obovate; scalloped with apex flat with one notch. Inside—obovate; scalloped with apex flat with one notch.

This description of a newly opened flower was made from a rose grown outdoors in the month of August, 1941, at West Grove, Pennsylvania:

*Color.* — Outside petal: outside surface — Primuline Yellow, Plate XVI, flushed and veined Tyrian Rose, Plate XII. Inside surface—Primuline Yellow, Plate XVI, flushed and veined Tyrian Rose, Plate XII. Intermediate petal: outside surface — Primuline Yellow, Plate XVI, flushed and veined Tyrian Rose, Plate XII. Inside surface—Primuline Yellow, Plate XVI, more heavily flushed and veined Tyrian Red, Plate XII. Inner petal: outside surface—Primuline Yellow, Plate XVI, more heavily flushed and veined Tyrian Red, Plate XII. Inside surface — Primuline Yellow, Plate XVI, more heavily flushed and veined Tyrian Red, Plate XII.

This description was made from a rose that was open for three days outdoors in the month of August, 1941, at West Grove, Pennsylvania:

*Color.*—Outside petal: outside surface—Primuline Yellow, Plate XVI, slightly flushed Tyrian Rose, Plate XII. Inside surface—Primuline Yellow, Plate XVI, veined and flushed Tyrian Rose, Plate XII. Inside petal: outside surface—Primuline Yellow, Plate XVI, slightly flushed Tyrian Rose, Plate XII. Inside surface—Primuline Yellow, Plate XVI, veined and flushed Tyrian Rose, Plate XII.
*General color effect.*—Newly opened flower—Glowing Tyrian Rose, Plate XII, and Salmon-Orange, Plate II. Three days open—Salmon-Orange, Plate II, flushed and veined Tyrian Pink, Plate XII.
*Behavior.*—Drop off cleanly; fading to multicolor Flesh Pink, Plate XIII, Deep Rose Pink, Plate XII, and Tyrian Pink, Plate XII.
*Flower longevity.*—On bush in garden—three to four days in August. Cut roses grown outdoors—three to five days in August.

*Reproductive organs*

Stamens: Medium number; arranged irregularly partly about pistils, mixed with petaloids.
Filaments: Short; Carmine, Plate I; most with anthers.
Anthers: Medium large; Salmon-Orange, Plate II; open at various times.
Pollen: Sparse; Orange-Buff, Plate III.
Pistils: Medium number.
Styles: Short; thin.
Stigma: Orange-Buff, Plate III.
Ovaries: All enclosed in calyx.
Hips: Globular with inconspicuous neck; Biscay Green, Plate XVII; smooth; walls thick, fleshy.
Sepals: Permanent; moderately long; spear-shaped; recurved.
Seeds: Very few; medium size.

*Plant*

Foliage:
*Leaves.*—Compound of three to five leaflets; normal; moderately large; leathery; glossy.
*Leaflets.*—*Shape*—ovoid with apex mucronate; base obtuse; margin simply serrate.
*Color.*—*Mature*—upper surface—Elm Green, Plate XVII. Under surface—Light Elm Green, Plate XVII. *Young*—upper surface—Olive-Citrine, Plate XVI, flushed Garnet-Brown, Plate I. Under surface—Garnet-Brown, Plate I, flushed Olive-Citrine, Plate XVI.
*Rachis.*—Medium heavy; upper side—grooved; under side—prickly; thorny.
*Stipules.*—Medium long; medium wide; moderately long points, turning out at an angle of less than 45°, recurved toward the stem.
*Disease.*—Resistant to mildew and blackspot.

Growth:
*Habit.*—Upright; much branched.
*Growth.*—Vigorous.
*Canes.*—Medium to heavy.
*Main stems.*—Dull Grass Green, Plate VI. *Thorns*—many; medium long; straight; with broad base. *Prickles*—none. *Hairs*—none.
*Branches.*—Grass Green, Plate VI. *Thorns*—several; medium long; straight; with narrow base. *Prickles*—none. *Hairs*—none.
*New shoots.*—Greenish Chestnut, Plate II. *Thorns*—several; medium long; straight; with narrow base. *Prickles*—none. *Hairs*—none.

I claim:

A new and distinct variety of Rose plant, characterized as to novelty by its great vigor of growth, the large size and novel color combination of its blooms giving rise to a multicolored effect of unusual attractiveness throughout their development from bud to full bloom, substantially as shown and described.

CHARLES MALLERIN.